United States Patent
Shuros et al.

(10) Patent No.: US 9,186,512 B2
(45) Date of Patent: Nov. 17, 2015

(54) METHOD AND APPARATUS FOR ORGAN SPECIFIC INFLAMMATION MONITORING

(75) Inventors: Allan C. Shuros, St. Paul, MN (US); Shantha Arcot-Krishnamurthy, Vadnais Heights, MN (US); Craig Stolen, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1029 days.

(21) Appl. No.: 12/565,233

(22) Filed: Sep. 23, 2009

(65) Prior Publication Data
US 2010/0076279 A1    Mar. 25, 2010

Related U.S. Application Data

(60) Provisional application No. 61/099,251, filed on Sep. 23, 2008.

(51) Int. Cl.
*A61N 1/365* (2006.01)
*A61N 1/362* (2006.01)
*A61B 5/00* (2006.01)
(Continued)

(52) U.S. Cl.
CPC ............ *A61N 1/3627* (2013.01); *A61B 5/0031* (2013.01); *A61B 5/01* (2013.01); *A61B 5/036* (2013.01); *A61B 5/053* (2013.01); *A61B 5/1076* (2013.01); *A61B 5/415* (2013.01); *A61B 5/416* (2013.01); *A61B 5/418* (2013.01); *A61B 5/4205* (2013.01); *A61B 5/4878* (2013.01); *A61B 8/488* (2013.01); *A61N 1/36521* (2013.01); *A61B 5/7275* (2013.01)

(58) Field of Classification Search
CPC .... A61B 5/053; A61B 5/418; A61N 1/36521; A61N 1/362
USPC .......... 600/301, 508, 481, 483, 309, 547, 549
See application file for complete search history.

(56) References Cited

U.S. PATENT DOCUMENTS 4,407,300 A     10/1983  Davis
5,243,976 A     9/1993   Ferek-Petric et al.
(Continued)

FOREIGN PATENT DOCUMENTS

JP       2012503499           2/2012
WO     WO-2005/032653 A1    4/2005
(Continued)

OTHER PUBLICATIONS

Akita, H., et al., "Electrophysiologic effects of intracellular lysophosphoglycerides and their accumulation in cardiac lymph with myocardial ischemia in dogs", *J Clin Invest.*, 78(1), (Jul. 1986), 271-80.

(Continued)

*Primary Examiner* — Tammie K Heller
(74) *Attorney, Agent, or Firm* — Schwegman Lundberg & Woessner, P.A.

(57) ABSTRACT

An apparatus comprises an implantable sensor and a detection circuit. The implantable sensor provides a physiologic sensor signal and is to be positioned at a lymph node of a subject. The detection circuit detects a change in a physiologic parameter of the lymph node that exceeds a threshold change, and deems that the change in the physiologic parameter indicates a change in inflammation of an organ associated with the lymph node.

25 Claims, 5 Drawing Sheets

(51) Int. Cl.
*A61B 5/01* (2006.01)
*A61B 5/03* (2006.01)
*A61B 5/053* (2006.01)
*A61B 5/107* (2006.01)
*A61B 8/08* (2006.01)

(56) References Cited

U.S. PATENT DOCUMENTS

| | | | |
|---|---|---|---|
| 5,882,352 | A | 3/1999 | Duncan et al. |
| 6,317,628 | B1 | 11/2001 | Linder et al. |
| 6,636,755 | B2 * | 10/2003 | Toida ........................... 600/407 |
| 6,666,826 | B2 | 12/2003 | Salo et al. |
| 6,738,663 | B2 | 5/2004 | Schroeppel et al. |
| 7,526,337 | B2 | 4/2009 | Shuros et al. |
| 2003/0028221 | A1 | 2/2003 | Zhu et al. |
| 2004/0049235 | A1 | 3/2004 | Deno et al. |
| 2004/0102712 | A1 | 5/2004 | Belalcazar et al. |
| 2004/0172075 | A1 | 9/2004 | Shafer et al. |
| 2004/0220637 | A1 | 11/2004 | Zdeblick et al. |
| 2004/0254618 | A1 | 12/2004 | Schroeppel et al. |
| 2004/0267142 | A1 | 12/2004 | Paul |
| 2005/0075701 | A1 * | 4/2005 | Shafer ........................... 607/72 |
| 2005/0222646 | A1 | 10/2005 | Kroll et al. |
| 2006/0287678 | A1 | 12/2006 | Shafer |
| 2007/0185535 | A1 | 8/2007 | Libbus et al. |
| 2007/0270675 | A1 | 11/2007 | Kane et al. |
| 2007/0276443 | A1 | 11/2007 | Shafer et al. |
| 2007/0282376 | A1 | 12/2007 | Shuros |
| 2007/0282382 | A1 | 12/2007 | Shuros et al. |
| 2007/0282386 | A1 | 12/2007 | Shuros |
| 2007/0282390 | A1 | 12/2007 | Shuros |
| 2008/0009719 | A1 | 1/2008 | Shuros et al. |
| 2008/0064954 | A1 | 3/2008 | Adams et al. |
| 2008/0097412 | A1 | 4/2008 | Shuros et al. |
| 2008/0140000 | A1 | 6/2008 | Shuros et al. |
| 2008/0140139 | A1 | 6/2008 | Heinrich et al. |
| 2008/0234556 | A1 | 9/2008 | Brooke et al. |
| 2008/0234772 | A1 | 9/2008 | Shuros et al. |
| 2008/0234774 | A1 | 9/2008 | Baynham et al. |
| 2008/0234792 | A1 | 9/2008 | Reddy |
| 2008/0294228 | A1 | 11/2008 | Brooke et al. |
| 2009/0012444 | A1 | 1/2009 | Shuros et al. |
| 2009/0082825 | A1 | 3/2009 | Arcot-Krishnamurthy et al. |
| 2009/0292212 | A1 * | 11/2009 | Ferren et al. ................. 600/481 |
| 2010/0256700 | A1 | 10/2010 | Shuros et al. |

FOREIGN PATENT DOCUMENTS

| | | |
|---|---|---|
| WO | WO-2007/131078 A2 | 11/2007 |
| WO | WO-2007/146489 A2 | 12/2007 |
| WO | WO-2010/039527 A1 | 4/2010 |
| WO | WO-2010/118033 A1 | 10/2010 |

OTHER PUBLICATIONS

Crowe, M. J., et al., "Co-ordination of contractile activity in guinea-pig mesenteric lymphatics", *Journal of Physiology*, 500(1), (1997), 235-244.

Drinker, C. K., et al., "The Flow, Pressure, and Composition of Cardiac Lymph", *American Journal of Physiology—Renal Physiology*, 130(1), (1940), 43-55.

Goldstein, R. S., et al., "Elevated High-Mobilitty Group Box 1 Levels in Patients With Cerebral and Myocardial Ischemia", *Shock*, 25(6), (2006), 571-574.

Miller, A. J, et al., "Cardiac lymph: flow rates and composition in dogs", *Am J Physiol.*, 206, (1964), 63-66.

Shuros, A. C., et al., "Method and Apparatus for Organ-Specific Inflammation Therapy", U.S. Appl. No. 61/167,280, filed Apr. 7, 2009, 23 pgs.

Theodorakis, G. N., et al., "Antiinflammatory Effects of Cardiac Resynchronization Therapy in Patients with Chronic Heart Failure", *Pacing and Clinical Electrophysiology*, 29(3), (2006), 255-261.

Vazquez-Jimenez, J. F., et al., "Cannulation of the Cardiac Lymphatic System in Swine", *European Journal of Cardio-Thoracic Surgery*, 18(2), (2000), 228-232.

Venugopal, A. M., et al., "Optimal Lymphatic Vessel Structure", *Proceedings of the 26th Annual International Conference of the IEEE Engineering in Medicine and Biology Society (IEMBS '04)*, (Sep. 1-5, 2004, San Francisco, CA), (2004), 3700-3703.

Yasuda, A., et al., "In situ observations of spontaneous contractions of the peripheral lymphatic vessles in the rat mesentery: Effects of temperature", *Experientia*, 40(4), (1984), 342-343.

Yndestad, A., et al., "Role of Inflammation in the Progression of Heart Failure", *Current Cardiology Reports*, 9(3), (2007), 236-241.

"International Application Serial No. PCT/US2009/058010, International Search Report mailed Feb. 1, 2010", 6 pgs.

"International Application Serial No. PCT/US2009/058010, Written Opinion mailed Feb. 1, 2010", 10 pgs.

"International Application Serial No. PCT/US 2010/030102, International Search Report mailed Jun. 29, 2010", 4 pgs.

"International Application Serial No. PCT/US2010/030102, Written Opinion mailed Jun. 29, 2010", 7 pgs.

Pastore, J. M., et al., "Triggered High-Output Pacing Therapy", U.S. Appl. No. 61/090,485, filed Aug. 20, 2008, 27 pgs.

"European Application No. 09792890.7, Office Action response filed Jan. 26, 2012", 13 pgs.

"European Application Serial No. 10713099.9, EPO Notice Amended Claims Due mailed Dec. 23, 2011", 2 pgs.

"European Application Serial No. 10713099.9, Response filed Jul. 2, 2012 to Office Action mailed Dec. 23, 2011", 10 pgs.

"U.S. Appl. No. 12/755,041, Non Final Office Action mailed Aug. 31, 2012", 11 pgs.

"U.S. Appl. No. 12/755,041, Final Office Action mailed Mar. 29, 2013", 13 pgs.

"U.S. Appl. No. 12/755,041, Response filed Nov. 30, 2012 to Non Final Office Action mailed Aug. 31, 2012", 7 pgs.

"Japanese Application Serial No. 2012-504781, Office Action mailed Apr. 17, 2013", With Partial Translation, 5 pgs.

"U.S. Appl. No. 12/755,041, Non Final Office Action mailed Jun. 19, 2014", 12 pgs.

"Application U.S. Appl. No. 12/755,041, Response filed 09-19-14 to Non Final Office Action mailed 06-19-14", 8 pgs.

"U.S. Appl. No. 12/755,041, Advisory Action mailed Apr. 16, 2015", 3 pgs.

"U.S. Appl. No. 12/755,041, Final Office Action mailed Jan. 9, 2015", 13 pgs.

"U.S. Appl. No. 12/755,041, Response filed Apr. 9, 2015 to Final Office Action mailed Jan. 9, 2015", 9 pgs.

* cited by examiner

METHOD AND APPARATUS FOR ORGAN SPECIFIC INFLAMMATION MONITORING

CLAIM OF PRIORITY

This non-provisional application claims the benefit of priority under 35 U.S.C. §119(e) to U.S. Provisional Patent Application Ser. No. 61/099,251, filed Sep. 23, 2008, the specification of which is herein incorporated by reference in its entirety.

BACKGROUND

Implantable medical devices (IMDs) include devices designed to be implanted into a patient or subject. Some examples of these devices include cardiac function management (CFM) devices such as implantable pacemakers and defibrillators or cardiac resynchronization therapy devices (CRTs), implantable devices with neural stimulation capability, implantable drug delivery systems, and implantable diagnostic devices.

The devices can be used to aid a physician or caregiver in patient diagnosis through internal monitoring of a patient's condition, which may include cardiac disease, or cardiomyopathy.

Congestive heart failure (HF) is a cardiac disease that causes the ventricles of the heart to have a reduced ability to contract which results in an inadequate amount of blood being pumped into circulation. Because blood is being pumped away from the lungs at a reduced rate, fluid may build up in a patient's lungs and cause difficulty in breathing. As a patient's condition worsens, the patient may develop a tendency to rest in an elevated posture to reduce the fluid buildup in his or her lungs. Some CRM devices provide electrical therapy to treat congestive heart failure.

Coronary artery disease is a cardiac disease that is commonly the underlying cause of ischemia. Ischemia occurs when blood flow to cardiac muscles decreases below the metabolic requirements of the heart. Detecting ischemia early is critical to the health of the patient and allows early initiation of treatment. Cardiac muscle cells that are ischemic are electrically irritable and may be more susceptible to abnormal heart rhythms (e.g., fibrillation). Further, ischemia impairs the pumping function of the heart. If left untreated the coronary artery disease may lead to myocardial infarction (i.e., heart attack).

OVERVIEW

This document relates generally to systems, devices, and methods for monitoring organ specific inflammation. In example 1, an apparatus includes an implantable sensor, configured to be positioned at a lymph node of a subject, that provides a physiologic sensor signal, and a detection circuit. The detection circuit detects a change in a physiologic parameter of the lymph node that exceeds a threshold change, and deems that the change in the physiologic parameter indicates a change in physiological status associated with the lymph node.

In example 2, the implantable sensor of example 2 is optionally configured to be positioned at a cardiac-associated lymph node of the subject. The detection circuit generates an indication of worsening cardiomyopathy according to the detected change in the physiologic parameter.

In example 3, the apparatus of examples 1 and 2 optionally includes a therapy circuit, communicatively coupled to the detection circuit, which provides a therapy to treat the cardiomyopathy. The detection circuit alters the therapy according to a detected change in the physiologic parameter.

In example 4, the implantable sensor of examples 1-3 is optionally included on a distal end of an implantable lead-sensor assembly. The implantable lead-sensor assembly includes a lead body shaped to mechanically bias the sensor against the lymph node.

In example 5, the implantable sensor of examples 1-4 is optionally included on a distal end of a transvenous electrode configured for placement in a blood vessel adjacent to the lymph node.

In example 6, the apparatus of examples 1-3 is optionally included in a leadless microelectronics device.

In example 7, the detection circuit of examples 1-6 optionally detects, using the physiologic sensor signal, a change in at least one of a change in size of the lymph node that exceeds a threshold size change, a change in pressure in the lymph node that exceeds a threshold pressure change, a change in a fluid content in the lymph node, and a change in flow rate of fluid in the lymph node.

In example 8, the implantable sensor of examples 1-7 optionally includes at least one of an acoustic transducer, an optical sensor, and a strain sensor.

In example 9, the implantable sensor of examples 1-8 optionally includes an implantable electrical impedance sensor to provide a sensor signal representative of electrical impedance of at least a portion of the lymph node. The detection circuit detects a change in the electrical impedance of the lymph node that exceeds a threshold impedance change.

In example 10, the implantable sensor of examples 1-9 optionally includes an implantable chemical sensor to provide a sensor signal representative of a cytokine concentration at the lymph node. The detection circuit detects a change in the cytokine concentration at the lymph node that exceeds a threshold concentration change.

In example 11, the implantable sensor of examples 1-10 optionally includes an implantable temperature sensor to provide a sensor signal representative of temperature of the lymph node. The detection circuit detects a change in temperature of the lymph node that exceeds a threshold temperature change.

In example 12, a system includes an implantable device and an external device. The implantable device comprises an implantable sensor, configured to be positioned at a lymph node of an organ of a subject, that provides a physiologic sensor signal, a first communication circuit to communicate information with another device; and a detection circuit, communicatively coupled to the implantable sensor and the first communication circuit, to detect a change in a physiologic parameter of the lymph node. The external device comprises a second communication circuit to communicate information with the implantable device, and a processor communicatively coupled to the second communication circuit. The processor receives information related to the change in the physiologic parameter of the lymph node and deems that the change in the physiologic parameter indicates a change physiologic status of the organ according to the change information.

In example 13, the processor of example 12 optionally generates trend information related to the change in the physiologic parameter of the lymph node, and generates an indication of progression of cancer according to the trend information.

In example 14, the processor of examples 12 and 13 optionally generates trend information related to the change in the physiologic parameter of the lymph node, and generates an indication of progression of cardiomyopathy according to the trend information.

In example 15, the processor of examples 12-14 optionally receives information related to systemic inflammation of the subject, and verifies a region of inflammation with the communicated lymph node information.

In example 16, a method includes providing an implantable sensor configured to be positioned at a lymph node of an organ of a subject, detecting a physiological change in the lymph node using the implantable sensor, and deeming that a change in inflammation of the organ occurred according to the physiological change in the lymph node.

In example 17, the providing an implantable sensor of example 16 optionally includes providing an implantable sensor configured to be positioned at a cardiac lymph node of the subject. The method of example 16 optionally includes providing an indication of worsening cardiomyopathy according to the detected change in the cardiac lymph node.

In example 18, the method of examples 16 and 17 optionally includes altering a device-based therapy to treat the cardiomyopathy according to a detected physiological change in the lymph node.

In example 19, the providing an implantable sensor of examples 16-18 optionally includes providing an implantable electrical impedance sensor, and the detecting a physiological change in the lymph node includes detecting a change in the electrical impedance of at least a portion of the lymph node.

In example 20, the providing an implantable sensor of examples 16-19 optionally includes providing an implantable acoustic transducer. The method includes receiving acoustic information at the transducer, and the detecting a physiological change in the lymph node includes detecting a change in the size of the lymph node using the acoustic information.

In example 21, the providing an implantable sensor of examples 16-20 optionally includes providing an implantable temperature sensor, and the detecting a physiological change in the lymph node includes detecting a change in temperature of the lymph node.

In example 22, the providing an implantable sensor of examples 16-21 optionally includes providing an implantable strain sensor, and the detecting a physiological change in the lymph node includes detecting a change in size of the lymph node using the implantable strain sensor.

In example 23, the providing an implantable sensor of examples 16-22 optionally includes providing an implantable chemical sensor, and the detecting a physiological change in the lymph node includes detecting a change in a concentration at the lymph node of at least one of cytokine, a metabolite, and a cardiac enzyme.

In example 24, the method of examples 16-23 optionally includes providing an indication of progression of cancer according to the detected change in the lymph node.

In example 25, the providing an implantable sensor of examples 16-24 optionally includes providing an implantable sensor integrated into a transvenous lead, and placing the sensor in a blood vessel adjacent to the lymph node.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document relates generally to systems, devices, and methods for monitoring organ specific inflammation. Monitoring inflammation of the heart may be used as a surrogate for monitoring cardiomyopathy. Chronic HF is a cardiomyopathy characterized in part by immune response activation and inflammation. Thus, patients with HF may have elevated levels of a number of inflammatory cytokines Coronary artery disease (atherosclerotic plaque) is also associated with inflammation. Metabolites, such as lysophosphatidylcholine (LPC) for example, accumulate in ischemic tissue. The accumulation is manifested as an increase in metabolite concentration that can influence the electrophysiologic abnormalities associated with ischemia.

The lymphatic system includes lymph tissue, nodes, and vessels. This system drains excess extravascular fluid. The physiologic properties or physical properties of a lymph node (e.g., size dimensions) are dynamic depending on the afferent flow. Monitoring the physiologic properties of a lymph node provides information about an organ associated with the lymph node.

Figure 1:
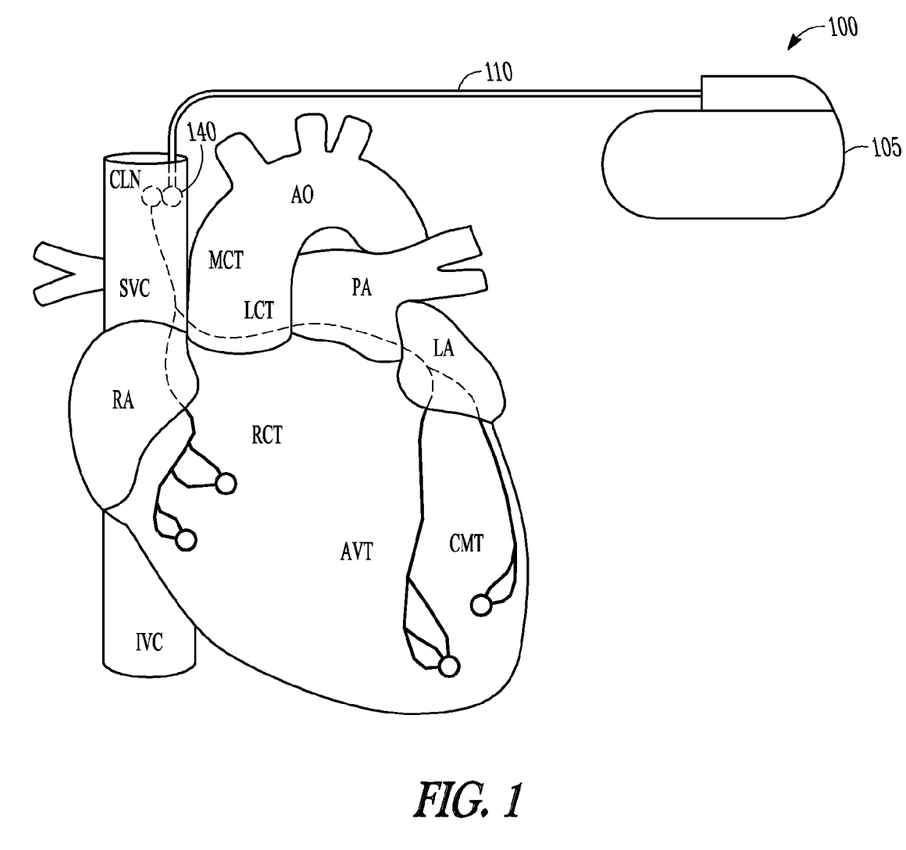
FIG. 1 is an illustration of a heart.

FIG. 1 includes an illustration of a porcine heart. Labeled in the illustration are the aorta (Ao), the superior vena cava (SVC), the inferior vena cava (IVC), the pulmonary artery (PA), the left atrium (LA), the right atrium (RA), the anterior interventricular trunk (AVT), the obtuse marginal trunk (OMT), the left coronary trunk (LCT), the right coronary trunk (RCT), the main coronary trunk (MCT), and a cardiac-associated lymph node (CLN). Interstitial fluid is absorbed from the myocardial tissue, filtered through the cardiac lymph node (CLN), and emptied into lymphatic vessels. Monitoring the physiologic properties of the cardiac lymph node provides information about health of the subject's heart. For example, an increase in size of the lymph node may indicate an increase in fluid flow due to inflammation of myocardial tissue. In another example, a change in concentration of the content of the fluid (lymph) may indicate inflammation or ischemia.

Other organs or organ systems that may be indirectly monitored by monitoring one or more lymph nodes associated with the organ include the brain, the kidneys, the gastrointestinal (GI) tract, the liver, spleen, and the pancreas.

Having enlarged lymph nodes is a symptom of a number of cancerous diseases such as Hodgkin lymphoma and leukemia for example. Other diseases associated with enlarged lymph nodes include reactive diseases such as acute infections (e.g., bacterial or viral) or chronic infections (e.g., tuberculous lymphadenitis or cat scratch disease), autoimmune etiology (e.g., sarcoidosis, systemic lupus erythematosus, or rheumatoid arthritis), or immunocompromised etiology (e.g., HIV and AIDS). Monitoring the physiologic properties of the cardiac lymph node (e.g., size or internal pressure) can be used to monitor progression of the disease.

Figure 2:
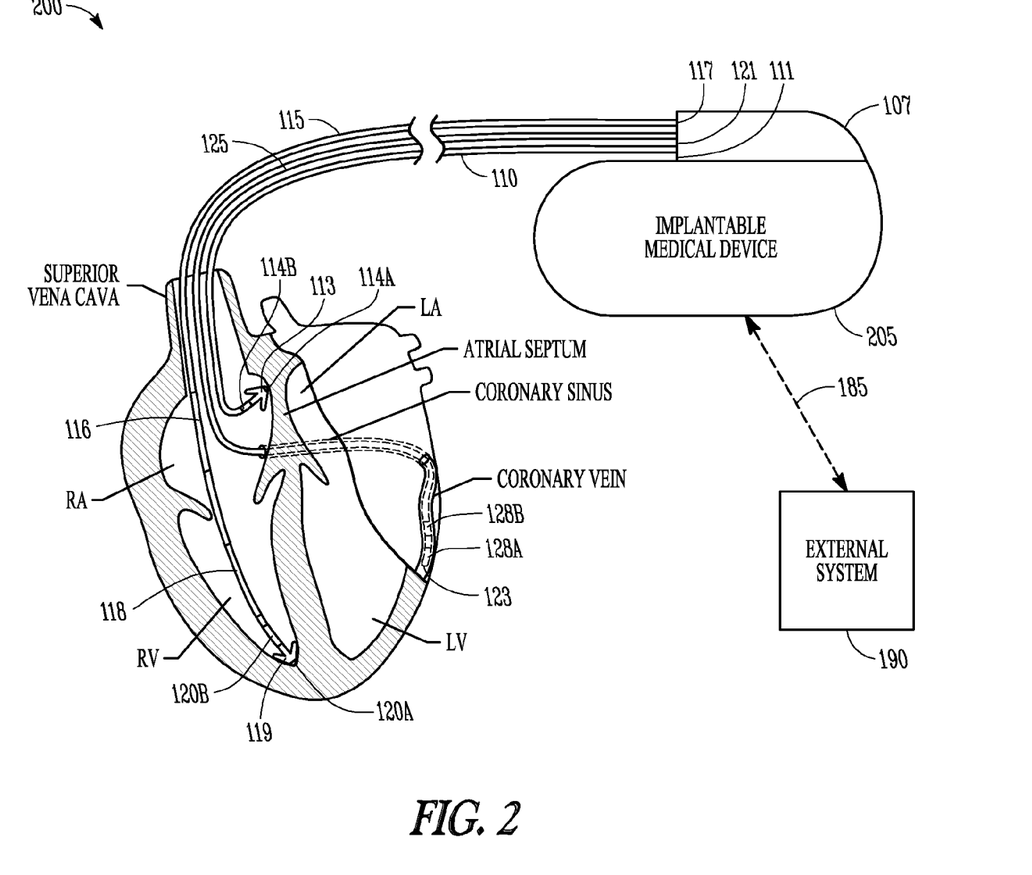
FIG. 2 is an illustration of portions of a system that uses an IMD.

FIG. 2 is an illustration of portions of a system 200 that uses an IMD 205. Examples of IMD 205 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 200 shown is used to treat a cardiac arrhythmia. The IMD 205 typically includes an electronics unit coupled by one or more cardiac leads 110, 115, 125, to a heart of a patient or subject. The electronics unit of the IMD 205 typically includes components that are enclosed in a hermetically-sealed canister or "can." The system 100 also typically includes an IMD programmer or other external system 190 that communicates one or more wireless signals 185 with the IMD 205, such as by using radio frequency (RF) or by one or more other telemetry methods.

The example shown includes right atrial (RA) lead 110 having a proximal end 111 and a distal end 113. The proximal end 111 is coupled to a header connector 107 of the IMD 205. The distal end 113 is configured for placement in the RA in or near the atrial septum. The RA lead 110 may include a pair of bipolar electrodes, such as an RA tip electrode 114A and an RA ring electrode 114B. The RA electrodes 114A and 114B are incorporated into the lead body at distal end 113 for placement in or near the RA, and are each electrically coupled to IMD 205 through a conductor extending within the lead body. The RA lead is shown placed in the atrial septum, but the RA lead may be placed in or near the atrial appendage, the atrial free wall, or elsewhere.

The example shown also includes a right ventricular (RV) lead 115 having a proximal end 117 and a distal end 119. The proximal end 117 is coupled to a header connector 107. The distal end 119 is configured for placement in the RV. The RV lead 115 may include one or more of a proximal defibrillation electrode 116, a distal defibrillation electrode 118, an RV tip electrode 120A, and an RV ring electrode 120B. The defibrillation electrode 116 is generally incorporated into the lead body such as in a location suitable for supraventricular placement in the RA and/or the superior vena cava. The defibrillation electrode 118 is incorporated into the lead body near the distal end 119 such as for placement in the RV. The RV electrodes 120A and 120B may form a bipolar electrode pair and are generally incorporated into the lead body at distal end 119. The electrodes 116, 118, 120A, and 120B are each electrically coupled to IMD 205, such as through one or more conductors extending within the lead body. The proximal defibrillation electrode 116, distal defibrillation electrode 118, or an electrode formed on the can of IMD 205 allow for delivery of cardioversion or defibrillation pulses to the heart.

The RV tip electrode 120A, RV ring electrode 120B, or an electrode formed on the can of IMD 205 allow for sensing an RV electrogram signal representative of RV depolarizations and delivering RV pacing pulses. In some examples, the IMD includes a sense amplifier circuit to provide amplification and/or filtering of the sensed signal. RA tip electrode 114A, RA ring electrode 114B, or an electrode formed on the can of IMD 205 allow for sensing an RA electrogram signal representative of RA depolarizations and allow for delivering RA pacing pulses. Sensing and pacing allows the IMD 205 to adjust timing of the heart chamber contractions. In some examples, the IMD 205 can adjust the timing of ventricular depolarizations with respect to the timing of atrial depolarizations by sensing electrical signals in the RA and pacing the RV at the desired atrial-ventricular (AV) delay time.

A left ventricular (LV) lead 125 can include a coronary pacing or sensing lead that includes an elongate lead body having a proximal end 121 and a distal end 123. The proximal end 121 is coupled to a header connector 107. A distal end 123 is configured for placement or insertion in the coronary vein. The LV lead 125 may include an LV ring or tip electrode 128A and an LV ring electrode 128B. The distal portion of the LV lead 125 is configured for placement in the coronary sinus and coronary vein such that the LV electrodes 128A and 128B are placed in the coronary vein. The LV electrodes 128A and 128B may form a bipolar electrode pair and are typically incorporated into the lead body at distal end 123. Each can be electrically coupled to IMD 205 such as through one or more conductors extending within the lead body. LV tip electrode 128A, LV ring electrode 128B, or an electrode formed on the can of the IMD 205 allow for sensing an LV electrogram signal representative of LV depolarizations and delivering LV pacing pulses.

An IMD may be configured with a variety of electrode arrangements, including transvenous, epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). An IMD may include one or more of the features, structures, methods, or combinations thereof described herein. An IMD may be implemented to provide a variety of therapeutic or diagnostic functions. Such a device may include implantable sensors for internal monitoring of physiological parameters of a patient. Physiological parameters include any measurable physical parameters or properties related to the physiology of the lymph node. These parameters include, among other things, size, temperature, internal pressure, fluid (lymph) content, fluid flow rate, lymph node cell composition, and the rate of change of lymph node cell composition.

Returning to FIG. 1, a system 100 that uses an IMD 105 is also shown. The IMD 105 shown has an implantable lead 110. Attached to the distal end of the lead is an implantable sensor 140. The implantable sensor 140 is deployed on or near the cardiac lymph node using a direct surgical approach or an indirect transvascular approach. A transvascular approach places the lead and sensor assembly inside the SVC in an area adjacent to the cardiac lymph node. This approach may require injection of a tracer (e.g., a barium injection in the myocardium) to allow fluoroscopic illumination of the cardiac lymph node. For monitoring other organs, the transvascular or transvenous approach places the implantable sensor 140 in a blood vessel adjacent an associated lymph node. In some examples, the implantable sensor 140 is implanted within a lymphatic vessel, such as the thoracic duct or a vessel branching from the thoracic duct.

In some examples, the IMD 105 includes multiple implantable sensors. These sensors may be attached to additional implantable leads. This allows the IMD 105 to monitor multiple lymph nodes. The lymph nodes monitored may be associated with multiple organs, or the lymph node monitored may by associated with the same organ to provide more comprehensive monitoring. In certain examples, multiple sensors are included on the same implantable lead. The sensors of the lead are placed within the lumen of the duct of the lymph node to provide translymphatic monitoring of the lymph node.

In some examples, if the implantable sensor is included on the distal end of an implantable lead-sensor assembly, the implantable lead-sensor assembly may include a lead body shaped to mechanically bias the sensor against the lymph node. This helps to ensure that the sensor maintains contact with the lymph node if that is important to the type of sensor in the implantable lead-sensor assembly.

In some examples, the system 100 including the implantable sensor 140 is assembled as a leadless implantable microelectronics device. The leadless implantable microelectronics device has a small size allowing placement of the device near or on the lymph node. An example of a leadless microelectronics device is an implantable bion microstimulator. A bion microstimulator is a miniature, implantable, self-contained device. Some bion microstimulators provide electrical stimulation therapy to treat various neurological disorders. The leadless implantable microelectronics device collects signals, data, or other information from the included implantable sensor and wirelessly communicates the information to an external device.

Figure 3:
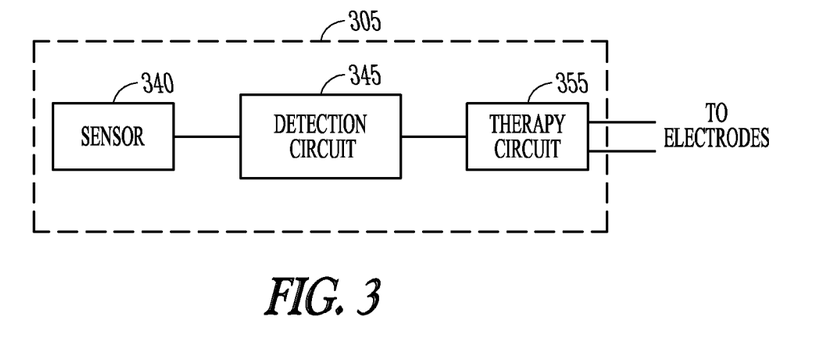
FIG. 3 is a block diagram of an example of an IMD to monitor a physiologic parameter of a lymph node.

FIG. 3 is a block diagram of an example of an IMD 305 to monitor a physiologic parameter of a lymph node. The IMD 305 includes an implantable sensor 340 and a detection circuit 345 communicatively coupled to the implantable sensor 340. Communicative coupling refers to devices arranged to communicate using electrical signals that influence the operation of the devices. In some examples, the devices are coupled directly. In some examples, the devices communicate electrical signals through intermediate devices, such as devices that include digital or analog circuits.

The implantable sensor 340 is configured for positioning at a lymph node of a subject, and the sensor provides a physiologic sensor signal that is representative of any of several physiologic parameters. A non-exhaustive list of the parameters include a size of the lymph node, a pressure of the lymph node, a content of the fluid (lymph) in the lymph node, a change in flow rate of fluid through the lymph node, a change in the composition or content of cells of the lymph node, and a rate of change of the composition of cells in the lymph node. Using the physiologic sensor signal, the detection circuit 345 detects a change in a physiologic parameter of the lymph node. When the change exceeds a threshold change value (e.g. the detected size exceeds a threshold size) or a threshold rate of change, the detection circuit 345 deems that the change in the physiologic parameter indicates a change in inflammation of an organ associated with the lymph node. In some examples, if the implantable sensor is configured to be positioned at a cardiac lymph node, the detection circuit 345 deems (according to the detected change in the physiologic parameter) whether the inflammation is indicative of progression of cardiomyopathy (e.g., HF or ischemia) and provides an indication of such progression, such as an indication of worsening cardiomyopathy for example.

In some examples, the detection circuit 345 includes a comparison circuit. The implantable sensor 340 provides an electrical signal (e.g., a voltage or current signal) representative of the physiologic parameter (e.g., size) of the lymph node. When the electrical signal provided to the comparison circuit exceeds a specified reference signal value, the comparison circuit provides an indication that the reference has been exceeded and the detection circuit 345 deems that the change is indicative of a change in the physiological status of the associated organ (e.g., a change in inflammation of the organ). In some examples, the detection circuit 345 includes a processor. The processor may include a digital signal processor, application specific integrated circuit (ASIC), microprocessor, or other type of processor, interpreting or executing instructions in software or firmware. The processor may include one or more modules to provide the functions described herein. A module may include software, hardware, firmware or any combination thereof. For example, the module may include instructions in software executing on or interpreted by the processor. Multiple functions may be performed by one or more modules.

Figure 4:
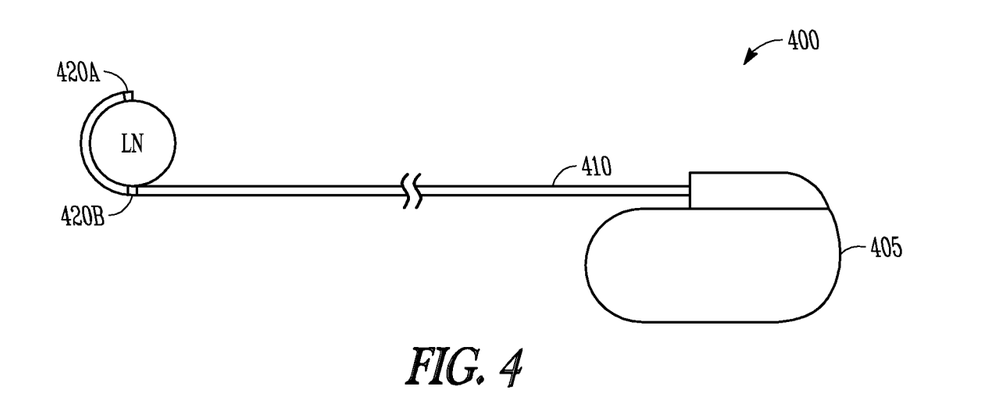
FIG. 4 is an illustration of a device to monitor a physiologic parameter of a lymph node.

FIG. 4 is an illustration of a device 400 to monitor a physiologic parameter of a lymph node. The device 400 monitors electrical impedance of at least a portion of a lymph node (LN) as a surrogate measurement of size or volume. The device shows an IMD 105 and an implantable electrical impedance sensor coupled by an implantable lead 410. The impedance sensor is placed near or next to a lymph node (LN).

The impedance sensor includes ring electrode 420B and electrode 420A which may be either a ring electrode or a tip electrode. To sense impedance of the lymph node, the IMD 405 injects a known current I between the electrodes 420A, 420B and senses the resulting voltage V between the electrodes 420A, 420B. Dividing the voltage by the current provides the impedance across the lymph node. In some examples, the impedance sensor includes four electrodes, and the IMD 405 injects current through a first pair of electrodes and senses current through a second pair of electrodes. An approach to monitoring impedance can be found in Linder et al, U.S. Pat. No. 6,317,628, entitled "Cardiac Rhythm Management System with Painless Lead Impedance Measurement System," filed Jan. 25, 1999, which is incorporated herein by reference in its entirety.

Returning to FIG. 3, as the lymph node expands due to increased fluid due to inflammation of an organ associated with lymph node, the measured impedance will decrease. The detection circuit 345 will detect when the measured impedance of the lymph node decreases below a specified impedance threshold value. When the threshold is satisfied, the detection circuit 345 deems that the change in the impedance corresponds to a change in size or to a change in fluid that indicates a change in inflammation of the organ.

The IMD 305 may include a different type of sensor, or sensors, to detect a change in size of a lymph node. In some examples, the implantable sensor 340 includes an implantable strain sensor (e.g., a strain gauge). The strain sensor is fixed next to the lymph node. In certain examples, the strain sensor includes a piezoelectric element. An increase in size of the lymph node causes stress on the strain sensor resulting in a change in voltage provided by the strain sensor. When the voltage exceeds a threshold value, the detection circuit 345 deems that the change in the voltage corresponds to a change in size that indicates a change in inflammation of the organ.

Figure 5:
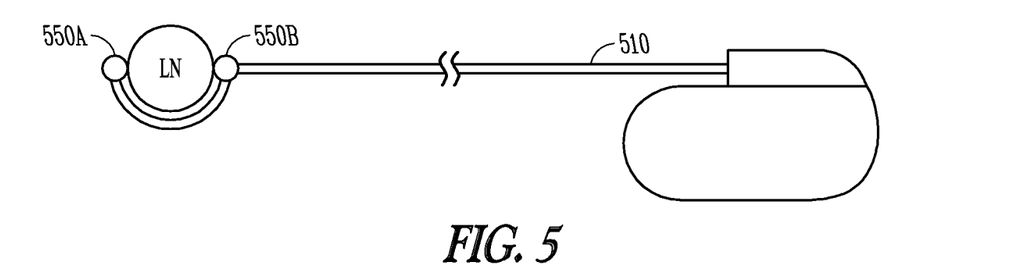
FIG. 5 shows an example of an implantable sensor having an acoustic transducer.

In some examples, the implantable sensor 340 includes an implantable acoustic transducer such as a Doppler ultrasonic transducer. FIG. 5 shows an example of an implantable sensor having an acoustic transducer. Two transducers 550A and 550B are placed near or next to the lymph node. In certain examples, the transducers 550A, 550B are included in an implantable lead 510. The first acoustic transducer generates ultrasonic energy having a frequency of about 2 MHz (megahertz) or higher, and the second acoustic transducer receives ultrasonic energy. The detection circuit 345 of FIG. 3 includes a Doppler circuit to receive ultrasonic acoustic information (e.g., wave or phase information) from the generated ultrasonic energy and measure the size of the lymph node using the Doppler Effect. The detection circuit 345 provides an indication when the measured size of the lymph node exceeds a threshold size.

In some examples, the Doppler circuit provides information as to the composition of cells. The Doppler circuit may measure the size of tissue that has a different composition of other cells in the lymph node (e.g., cancer cells). The Doppler circuit may be used to monitor the rate of the change in size (e.g., growth) of such lymph node tissue.

In some examples, the implantable sensor 340 includes an optical sensor. In certain examples, a light source is placed opposite the lymph node from the optical sensor which is communicatively coupled to the detection circuit 345. Instead of ultrasonic energy, the detection circuit 345 detects a phase shift in the incident light to determine a change in size of the lymph node. In certain examples, the light source is an infrared light source.

In some examples, the physiologic parameter monitored includes the temperature of the lymph node. The implantable sensor 340 includes an implantable temperature sensor that provides a sensor signal representative of temperature of the lymph node. The detection circuit 345 detects a change in temperature of the lymph node that exceeds a threshold temperature change and deems that the change indicates a change in inflammation of the associated organ.

In some examples, the physiologic parameter monitored includes the pressure of the lymph node. An increase in internal pressure of the lymph node may be the result of an increase in fluid drainage due to inflammation of the associated organ. The implantable sensor 340 includes an implantable pressure sensor to measure internal pressure of the lymph node. A description of systems and methods that use such an implantable pressure sensor is found in Salo et al., U.S. Pat. No. 6,666,826, entitled "Method and Apparatus for Measuring Left Ventricular Pressure," filed Jan. 4, 2002, which is incorporated herein by reference.

In some examples, the physiologic parameter monitored includes a rate of flow of lymph fluids. In certain examples, the previously mentioned Doppler ultrasonic transducer can be used to measure fluid flow rate. The detection circuit 345 includes a Doppler circuit to receive ultrasonic information (e.g., wave or phase information) having a frequency of 2 MHz or higher to measure the fluid velocity using the Doppler Effect. The Doppler circuit generates a blood flow velocity measurement from the ultrasonic information. The detection circuit 345 may include a signal processor to generate the fluid flow velocity measurement. A description of measuring blood flow velocity using the Doppler Effect is found in Ferek-Petric et al., U.S. Pat. No. 5,243,976, "Tricuspid Flow Synchronized Cardiac Electrotherapy System with Blood Flow Measurement Transducer and Controlled Pacing Signals Based on Blood Flow Measurement," filed Mar. 25, 1991, which is incorporated herein by reference in its entirety.

In certain examples, the rate of flow can be monitored using thermal dilution. Heat can be added to the lymph node, such as by ultrasound for example. The heat dissipation can be monitored using the previously mentioned temperature sensor.

In some examples, the physiologic parameter monitored includes the chemical content of the fluid of the lymph node. Pro-inflammatory cytokines have been correlated to the severity of heart failure. The implantable sensor 340 includes an implantable chemical sensor. In certain examples, the implantable chemical sensor provides a sensor signal representative of a cytokine concentration at the lymph node. The detection circuit 345 detects a change in the cytokine concentration at the lymph node that exceeds a threshold concentration change.

In certain examples, the implantable chemical sensor provides a sensor signal representative of metabolites such as lysophoglycerides (LPC) in the lymph node fluid. In certain examples, the implantable chemical sensor provides a sensor signal representative of cardiac enzymes like troponins. Changes in levels of metabolites and cardiac enzymes have been associated with ischemia. In some examples, the detection circuit 345 provides an indication of ischemia according to a detected change in concentration of at least one of a metabolite and a cardiac enzyme in the lymph node fluid.

In some examples, the implantable chemical sensor includes a blood chemical sensor. Illustrative examples include a blood electrolyte sensor, such as to provide a sensor signal corresponding to one or more of a level of potassium (K), sodium (Na), calcium (Ca), glucose, or creatinine. In some examples, the blood chemical sensor provides a signal representative of blood pH. An example of an approach to providing a chemical sensor is found in Kane et al., U.S. patent application Ser. No. 11/383,933, entitled, "Implantable Medical Device with Chemical Sensor and Related Methods," filed May 17, 2006, which is incorporated herein by reference.

Figure 6:
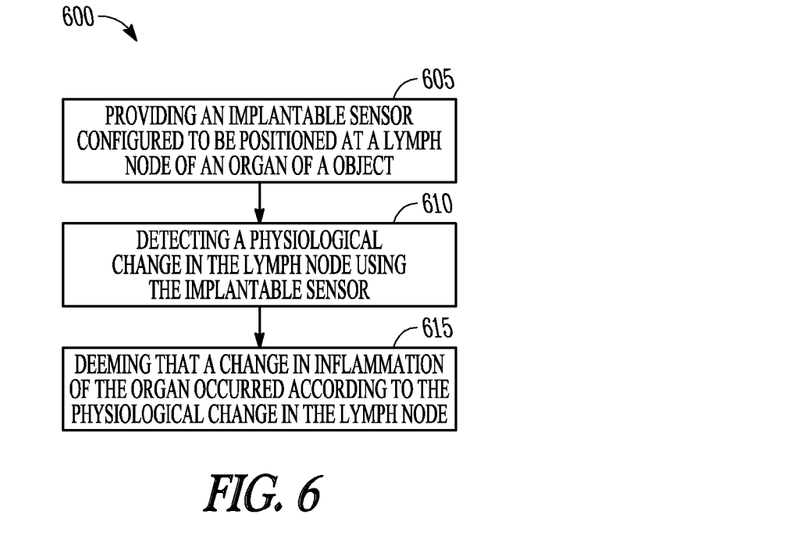
FIG. 6 is a flow diagram of an example of a method to monitor a physiologic parameter of a lymph node.

FIG. 6 is a flow diagram of an example of a method 600 to monitor a physiologic parameter of a lymph node. At block 605, an implantable sensor is provided. The implantable sensor is configured to be positioned at a lymph node of an organ of a subject. At block 610, a physiological change is detected in the lymph node using the implantable sensor. At block 615, a change in physiological status of the organ is deemed to have occurred according to the physiological change in the lymph node. In some examples, the change in physiological status includes a change in inflammation of the organ.

Returning to FIG. 3, in some examples, the IMD 305 includes a therapy circuit 355 communicatively coupled to the detection circuit 345. The therapy circuit 355 provides a therapy to treat the cardiomyopathy. In some examples, the therapy circuit 355 provides electrical stimulation therapy such as pacing therapy or neuro-stimulation therapy. Pacing therapy such as cardiac resynchronization therapy (CRT) may reduce the amount of pro-inflammatory cytokines. In some examples, the therapy circuit 355 provides titration of one or more pharmacological agents to the patient.

The detection circuit 345 alters the therapy provided by the therapy circuit 355 according to a detected change in the physiologic parameter. In an illustrative example, the therapy circuit 355 provides CRT and the implantable sensor includes a chemical sensor that can detect cytokines. The detection circuit 345 may alter the CRT to alter the inflammation in the organ using the output of the chemical sensor as feedback to the effectiveness of the changed CRT regimen. If the inflammation is related to an ischemic episode of the patient, the detection circuit 345 may alter tachyarrhythmia detection parameters. Conversely, a change in inflammation may provide feedback as to the efficacy of the CRT. Thus, the inflammation monitoring can be used to optimize the CRT therapy.

In some examples, the detection circuit 345 may provide recommendations to alter one or more CRT parameters. These recommendations may be communicated to an external device (e.g., an IMD programmer) for review by a clinician or physician. The clinician may then choose to adopt the recommendations of the device or the clinician may program their own alternative parameters into the IMD 305 using information communicated from the IMD 305.

Figure 7:
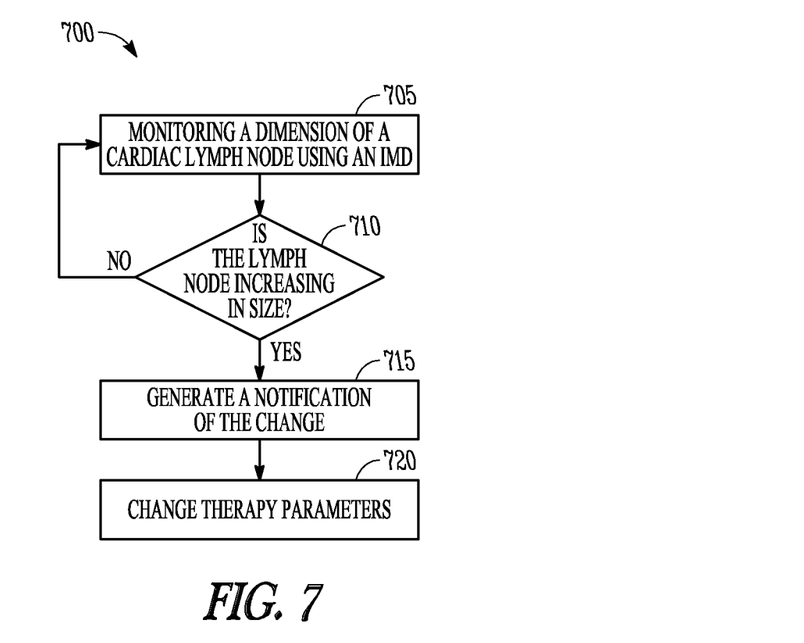
FIG. 7 is a flow diagram of another example of a method to monitor a physiologic parameter of a lymph node.

FIG. 7 is a flow diagram of another example of a method 700 to monitor a physiologic parameter of a lymph node. In the example, the lymph node monitored is a cardiac lymph node. At block 705, the IMD monitors a physiologic parameter of the lymph node. In the example, the parameter monitored is a size dimension of the lymph node. At block 710, it is determined whether the lymph node is increasing in size. If not, the monitoring continues at block 705.

At block 715, a notification of the change is generated if the size is increasing. In some examples, the notification is transmitted to a second external device for display. In some examples, the notification is communicated to an advanced patient management system to provide notification to health care personnel.

At block 720, device-based therapy parameters are changed in response to the detected change in the lymph node. In some examples, the IMD is a cardiac function management (CFM) device and one or more CFM parameters are changed. In certain examples, one or more parameters related to pacing therapy are changed. In certain examples, tachyarrhythmia detection parameters are changed, such as decreasing a tachyarrhythmia detection rate zone or shortening a detection time duration for example. In certain examples, the IMD is a neuron-stimulation device and one or more neuron-stimulation parameters are changed.

Figure 8:
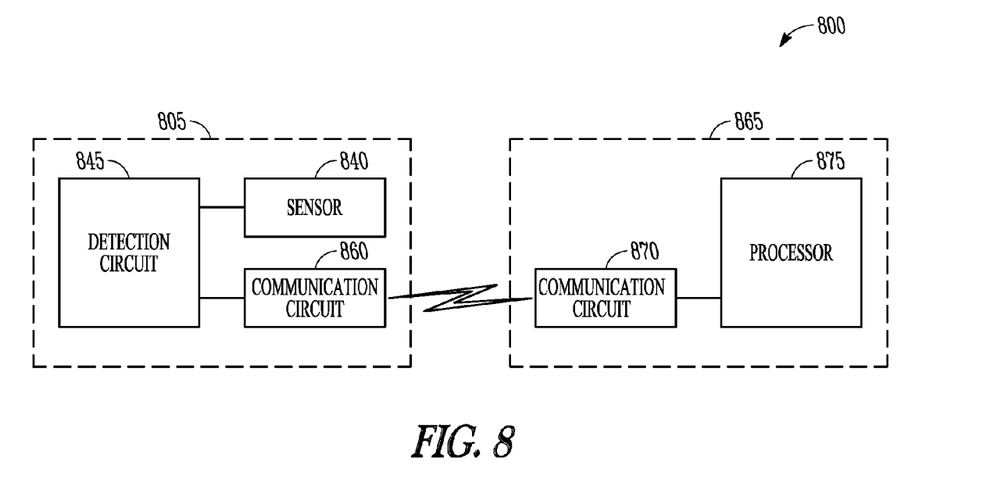
FIG. 8 is a block diagram of an example of a system to monitor a physiologic parameter of a lymph node.

FIG. 8 is a block diagram of an example of a system 800 to monitor a physiologic parameter of a lymph node. The system 800 includes an implantable device 805 and an external device 865. The implantable device includes an implantable sensor 840, a detection circuit 845, and a first communication circuit 860. The implantable sensor 840 is positioned at the lymph node for the monitoring and provides a physiologic sensor signal. The detection circuit 845 is communicatively coupled to the implantable sensor 840 and the first communication circuit 860 and detects a change in a physiologic parameter of the lymph node. The first communication circuit 860 communicates information wirelessly with another device, such as the external device 865. In certain examples, the implantable device 805 communicates with other implantable devices using the first communication circuit 860.

The external device 865 includes a second communication circuit 870 to communicate information with the implantable device 805. The external device 865 also includes a processor 875 communicatively coupled to the second communication circuit 870. The processor 875 may include a digital signal processor, application specific integrated circuit (ASIC), microprocessor, or other type of processor, interpreting or executing instructions in software or firmware. The external device 865 may be a programmer of the implantable device 805, or may be a repeater to relay information between the implantable device 805 and a third device. In certain examples, the external device 865 may be a server receiving information from the implantable device 805 via a repeater.

The processor 875 receives information related to the change in the physiologic parameter of the lymph node from the implantable device 805 and, using the information, deems whether the change in the physiologic parameter indicates a change in inflammation of the organ according to the change information. The processor 875 may generate a notification of the change in inflammation. In some examples, the processor 875 may generate a prompt or alert that recommends that the physician or clinician execute another patient test.

In some examples, the functions related to monitoring the physiologic parameter of the lymph node are split between the implantable device 805 and the external device 865. Assume the physiologic parameter monitored includes a rate of flow of lymph fluids. The previously mentioned Doppler ultrasonic transducer may be included in the implantable device 805. The ultrasonic information is communicated to the external device 865 which includes the Doppler circuit to measure the fluid velocity using the Doppler Effect. The processor 875 may be a signal processor that generates the fluid flow velocity measurement.

In some examples, the external device 865 includes a memory to store the information from the implantable device 805. The processor 875 generates trend information related to the change in the physiologic parameter of the lymph node. Based on the trend information, the processor 875 generates an indication of progression of the cardiomyopathy. In certain examples, the processor 875 generates an indication of progression of cancer according to the trend information. In certain examples, the implantable device 805 includes a memory to trend the information related to the change in the physiologic parameter and communicates the indication of progression of the cardiomyopathy or the progression of cancer to the external device 865.

In some examples, the external device 865 may have access to health related information of the subject from other sources. The external device 865 may communicate with other device over a computer network such as the internet. The physiologic information related to the lymph node may be used in conjunction with the other health related information to manage the subject's disease. For example, the processor 875 may receive information related to systemic inflammation of the subject. This information may be received from a server connected to the computer network. The external device 865 uses the information related to the change in the physiologic parameter of the lymph node to verify a region of inflammation in the subject. For example, if the lymph node is associated with the heart, the information can be used to verify whether the inflammation is systemic or if the inflammation is cardiac in nature.

In some examples, the physiologic information related to the lymph node may be used in conjunction with other patient tests. For example, if information from the implantable device 805 leads to an indication of a change in inflammation of the associated organ, the external device may initiate a biomarker assay test. Depending on the form of the system, the indication of the change may come from the implantable device 805 or may be generated by the external device 865. This indication of a change in homeostasis would lead the external device 865 to provide a prompt to the patient or clinician for the test. The test may include providing the external device 865 with some blood for assaying, or may include providing the results of the assay to the external device 865 via a user interface.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
    an implantable sensor configured to be positioned at a lymph node of a subject, wherein the implantable sensor provides a physiologic sensor signal;
    a therapy circuit configured to provide one or more of cardiac pacing therapy, cardiac resynchronization therapy, cardioversion therapy, and cardiac defibrillation therapy; and
    a detection circuit configured to:
        detect a change in a physiologic parameter of the lymph node that exceeds a threshold change wherein the change in the physiologic parameter includes at least one of a change in the electrical impedance of the lymph node that exceeds a threshold impedance change and a change in at least one of a change in size of the lymph node that exceeds a threshold size change;
        generate an indication that the change in the physiologic parameter corresponds to a change in physiological status associated with the lymph node; and
        adjust a parameter of the one or more of cardiac pacing therapy, cardiac resynchronization therapy, cardioversion therapy; and cardiac defibrillation therapy in response to the generated indication.

2. The apparatus of claim 1, wherein the implantable sensor is configured to be positioned at a cardiac-associated lymph node of the subject, and wherein the detection circuit is configured to generate an indication of worsening cardiomyopathy according to the detected change in the physiologic parameter.

3. The apparatus of claim 2,
    wherein the therapy circuit is configured to provide a therapy to treat the cardiomyopathy, and
    wherein the detection circuit is configured to alter the therapy according to a detected change in the physiologic parameter.

4. The apparatus of claim 1, wherein the implantable sensor is included on a distal end of an implantable lead-sensor assembly, wherein the implantable lead-sensor assembly includes a lead body shaped to mechanically bias the sensor against the lymph node.

5. The apparatus of claim 1, wherein the implantable sensor is included on a distal end of a transvenous electrode configured for placement in a blood vessel adjacent to the lymph node.

6. The apparatus of claim 1, wherein the apparatus is included in a leadless microelectronics device.

7. The apparatus of claim 1, wherein the detection circuit is configured to detect, using the physiologic sensor signal, at least one of a change in pressure in the lymph node that exceeds a threshold pressure change, and a change in flow rate of fluid in the lymph node.

8. The apparatus of claim 1, wherein the implantable sensor includes at least one of an acoustic transducer, an optical sensor, and a strain sensor.

9. The apparatus of claim 1, wherein the detection circuit is configured to detect a change in fluid content in the lymph node using the physiologic sensor signal.

10. The apparatus of claim 1, wherein the implantable sensor includes an implantable chemical sensor configured to provide a sensor signal representative of a cytokine concentration at the lymph node, and wherein the detection circuit is configured to detect a change in the cytokine concentration at the lymph node that exceeds a threshold concentration change.

11. The apparatus of claim 1, wherein the implantable sensor includes an implantable temperature sensor configured to provide a sensor signal representative of temperature of the lymph node, and wherein the detection circuit is configured to detect a change in temperature of the lymph node that exceeds a threshold temperature change.

12. A system comprising:
    an implantable device comprising:
        an implantable sensor configured to be positioned at a lymph node of an organ of a subject, wherein the implantable sensor provides a physiologic sensor signal;
        a therapy circuit configured to provide one or more of cardiac pacing therapy, cardiac resynchronization therapy, cardioversion therapy, and cardiac defibrillation therapy;

a first communication circuit configured to communicate information with another device; and
a detection circuit, communicatively coupled to the implantable sensor and the first communication circuit, configured to detect a change in a physiologic parameter of the lymph node wherein the change in the physiologic parameter includes at least one of a change in the electrical impedance of the lymph node that exceeds a threshold impedance change, and a change in size of the lymph node that exceeds a threshold size change; and
an external device comprising:
a second communication circuit configured to communicate information with implantable device; and
a processor, communicatively coupled to the second communication circuit, configured to:
receive information related to the change in the physiologic parameter of the lymph node;
generate an indication that the change in the physiologic parameter corresponds to a change in a physiologic status of the organ according to the change information; and
initiate an adjustment to a parameter of one or more of cardiac pacing therapy, cardiac resynchronization therapy, cardioversion therapy, and cardiac defibrillation therapy in response to the generated indication.

13. The system of claim 12, wherein the processor is configured to:
generate trend information related to the change in the physiologic parameter of the lymph node; and
generate an indication of progression of cancer according to the trend information.

14. The system of claim 12, wherein the processor is configured to:
generate trend information related to the change in the physiologic parameter of the lymph node; and
generate an indication of progression of cardiomyopathy according to the trend information.

15. The system of claim 12, wherein the processor is configured to:
receive information related to systemic inflammation of the subject; and
verify a region of inflammation with the communicated lymph node information.

16. A method comprising:
detecting a change in a physiological parameter of a lymph node of an organ of a subject that exceeds threshold change using an implantable sensor configured to be positioned at the lymph node, wherein the change in the physiologic parameter includes at least one of a change in the electrical impedance of the lymph node that exceeds a threshold impedance change, and a change in size of the lymph node that exceeds a threshold size change;
generating an indication of a change in a physiological stains of the lymph node according to the detected change in the physiological parameter of the lymph node; and
adjusting, in response to the generated indication, one or more of cardiac pacing therapy, cardiac resynchronization therapy, cardioversion therapy, and cardiac defibrillation therapy provided to the subject.

17. The method of claim 16, wherein using an implantable sensor includes providing an implantable sensor configured to be positioned at a cardiac lymph node of the subject, and wherein the method includes providing an indication of worsening cardiomyopathy according to the detected change in the cardiac lymph node.

18. The method of claim 17, wherein adjusting excitatory cardiac stimulation therapy includes adjusting excitatory cardiac stimulation therapy to treat the cardiomyopathy according to a detected physiological change in the lymph node.

19. The method of claim 16, wherein detecting a change using an implantable sensor includes detecting the change using an implantable pressure sensor, and wherein detecting a change in a physiological parameter of the lymph node includes detecting a change in pressure in the lymph node.

20. The method of claim 16,
wherein detecting a change using an implantable sensor includes detecting the change using an implantable acoustic transducer,
wherein the method includes receiving acoustic information at the transducer, and
wherein detecting a change in a physiological parameter of the lymph node includes detecting the change in the size of the lymph node using the acoustic information.

21. The method of claim 16, wherein detecting a change using an implantable sensor includes detecting the change using an implantable temperature sensor, and wherein detecting a change in a physiological parameter of the lymph node includes detecting a change in temperature of the lymph node.

22. The method of claim 16, wherein detecting a change using an implantable sensor includes detecting the change using an implantable strain sensor, and wherein detecting a change in a physiological parameter of the lymph node includes detecting the change in size of the lymph node using the implantable strain sensor.

23. The method of claim 22, wherein detecting a change using an implantable sensor includes detecting the change using an implantable chemical sensor, and wherein detecting a change in a physiological parameter of the lymph node includes detecting a change in a concentration at the lymph node of at least one of cytokine, a metabolite, and a cardiac enzyme.

24. The method of claim 23, including providing an indication of progression of cancer according to the detected change in the lymph node.

25. The method of claim 16, wherein detecting a change using an implantable sensor includes detecting the change using an implantable sensor integrated into a transvenous lead wherein the implantable sensor is configured for placement in a blood vessel adjacent to the lymph node.

* * * * *